United States Patent [19]
Voudouris

[11] Patent Number: 5,908,293
[45] Date of Patent: Jun. 1, 1999

[54] ORTHODONTIC BRACKET

[76] Inventor: John C. Voudouris, 16 Doon Rd., Toronto, Ontario, Canada, M2L1L9

[21] Appl. No.: 08/833,069

[22] Filed: Apr. 3, 1997

Related U.S. Application Data

[63] Continuation-in-part of application No. 08/745,512, Dec. 23, 1996, which is a continuation-in-part of application No. 08/625,944, Apr. 1, 1996, Pat. No. 5,857,850, which is a continuation-in-part of application No. 08/412,338, Mar. 31, 1995, abandoned, which is a continuation-in-part of application No. 08/206,724, Mar. 7, 1994, Pat. No. 5,474,445.

[30] Foreign Application Priority Data

Mar. 31, 1995 [GB] United Kingdom .................... 9506696

[51] Int. Cl.⁶ ...................................................... A61C 3/00
[52] U.S. Cl. ................................. 433/10; 433/11; 433/14
[58] Field of Search .................................. 433/8, 10, 11, 433/13, 14, 9

[56] References Cited

U.S. PATENT DOCUMENTS 3,922,787  12/1975  Fischer et al. .............................. 433/15
4,103,423  8/1978  Kessel ......................................... 433/10
4,634,662  1/1987  Rosenberg ................................. 433/10

FOREIGN PATENT DOCUMENTS

3700517  8/1987  Germany .................................. 433/13

*Primary Examiner*—John J. Wilson
*Attorney, Agent, or Firm*—Synnestvedt & Lechner LLP

[57] ABSTRACT

A pre-engaging orthodontic bracket for attaching an archwire to a tooth includes a body having a lingual surface for attachment to the tooth, a pair of laterally spaced gingival tie wings and a pair of laterally spaced occlusal tie wings. The gingival and occlusal tie wings project from a labial surface of the body. The gingival and occlusal tie wings are separated by an interwing region of the body. An archwire slot extends mesiodistally across the body between the gingival and occlusal tie wings to accommodate and archwire. A locking shutter is pivotally mounted about at least one pivot pin on the body between an open position in which placement and removal of an archwire in the archwire slot is facilitated and a closed position in which placement of the archwire in the archwire slot is inhibited. Alternative embodiments of a pre-engaging orthodontic brackets are also disclosed.

22 Claims, 10 Drawing Sheets

ORTHODONTIC BRACKET

RELATED APPLICATIONS

The present application is a continuation-in-part of U.S. application Ser. No. 08/745,512, filed on Dec. 23, 1996 which is a continuation-in-part of U.S. application Ser. No. 08/625,944, filed on Apr. 1, 1996, now U.S. Pat. No. 5,857,850, which is a continuation-in-part of U.S. application Ser. No. 08/412,338 filed on Mar. 31, 1995 now abandoned which is a continuation-in-part of U.S. application Ser. No. 08/206,724 filed on Mar. 7, 1994 now issued and granted under U.S. Pat. No. 5,474,445.

FIELD OF THE INVENTION

The present invention relates in general to orthodontic brackets and in particular to a pre-engaging orthodontic bracket for attaching an archwire to a tooth.

BACKGROUND OF THE INVENTION

According to established orthodontic techniques, it is well known that one is able to ligate an archwire to an orthodontic bracket utilizing an elastic, elastomeric or metal ligature. In a twin edgewise orthodontic bracket, the elastic ligature is stretched around respective undercuts of gingival and occlusal tie wings so as to overlay the archwire at mesial and distal ends of the orthodontic bracket.

The ligating procedure involves carefully stretching the elastic or elastomeric ligature (or wrapping and twisting a metal ligature) around the tie wings utilizing appropriate orthodontic instruments. It has been found that the time-consuming ligation procedure contributes to lengthy chair time. Furthermore, the elastic ligatures are known to lose their elasticity with time and are subject to degradation. In addition, the elastic and metal ligatures tend to trap food particles in areas of the orthodontic bracket which are difficult for the patient to clean. Also, the elastic and metal ligatures increase the level of friction against the archwire. Furthermore, the use of sharp metal ligatures around the orthodontic bracket subject the clinician to unnecessary exposure to infectious bacteria, or viruses such as hepatitis B, or possibly the HIV virus particularly in blood.

In an effort to overcome these disadvantages associated with elastic and metal ligatures, certain advances have been made in the area of pre-engaging orthodontic brackets. Each of U.S. Pat. Nos. 4,144,642; 4,248,588; 4,698,017; 3,772,787; 4,786,242; 4,559,012; 4,561,844; 4,655,708; 4,077,126; 4,419,078; 4,634,661; 4,197,642; and 4,712,999 illustrate one or more designs of pre-engaging brackets. The pre-engaging orthodontic brackets disclosed in these patents overcome some of the disadvantages associated with elastic and metal ligatures.

For example, pre-engaging orthodontic brackets eliminate, or at least reduce, exposure of the clinician to sharp metal ligatures, thereby alleviating the problem of contracting harmful bacteria or viruses. In addition, pre-engaging orthodontic brackets permit continuous low deflection differential archwire contact separately for both round and rectangular archwires at at least two different levels of contact, which is not possible with degrading elastic, elastomeric or rigid, high deflection metal ligatures. However, most of the known prior art pre-engaging orthodontic brackets lack the reliability and the accessible case of operability that most clinicians require. In addition, the majority of prior art pre-engaging orthodontic brackets are of a single design that have three or fewer tie wings.

It is therefore an object of the present invention to provide novel pre-engaging orthodontic brackets which obviate or mitigate at least one of the above-identified disadvantages associated with prior art pre-engaging orthodontic brackets.

SUMMARY OF THE INVENTION

According to one aspect of the present invention there is provided a pre-engaging orthodontic bracket for attaching an archwire to a tooth comprising:

a body having a lingual surface for attachment to a tooth, a pair of laterally spaced gingival tie wings and a pair of laterally spaced occlusal tie wings, said gingival and occlusal tie wings projecting from a labial surface of said body, both said gingival tie wings and occlusal tie wings at opposed mesial and distal sides of said body being separated by an interwing region of said body;

an archwire slot extending mesiodistally across said body and between the gingival and occlusal tie wings to accommodate an archwire; and a locking shutter pivotal about at least one pivot pin between an open position in which placement and removal of said archwire in said archwire slot is facilitated and a closed position in which placement of said archwire in said archwire slot is inhibited.

Preferably, the locking shutter includes a pair of laterally spaced flanges thereon, each of the flanges overlying a side surface of a respective one of one of the pairs of tie wings. The flanges accommodate pivot pins extending from the one pair of tie wings. It is also preferred that the orthodontic bracket further includes a locking mechanism to retain the locking shutter in the closed position. Preferably, the locking mechanism is in the form of a spring element mounted on the body with the spring element being pivotable to surround a gingival extension on the locking shutter and retain the locking shutter in the closed position.

In one embodiment, the spring element is generally triangular and is pivotally mounted on a gingival extension on the body adjacent the lingual surface. The spring element has in-turned mesial and distal ends accommodated by bores in the gingival extension. The in-turned ends are generally horizontal and are vertically are offset with respect to one another.

In another embodiment, the locking shutter includes a gingival arm overlying a gingival surface of the body when the locking shutter is in the closed position. The locking mechanism in this case is in the form of a retainer extending gingivally from the gingival surface. The retainer is accommodated by a hole in the gingival arm of the locking shutter when the locking shutter is in the closed position. Preferably, the retainer is accommodated within a passage formed in the body and is biased towards the gingival surface by a spring within the passage. The retainer has a nipple thereon extending beyond the passage and is accommodated by the hole in the locking shutter when the locking shutter is in the closed position.

According to another aspect of the present invention there is provided a pre-engaging orthodontic bracket for attaching an archwire to a tooth comprising:

a body having a lingual surface for attachment to a tooth, at least one gingival tie wing and at least one occlusal tie wing, said gingival and occlusal tie wings projecting from a labial surface of said body;

an archwire slot extending mesiodistally across said body between said gingival and at least one occlusal tie wing to accommodate an archwire; and a locking shutter in the form of a spring element pivotally mounted on said body, said spring element being pivotable between an open position in which placement and removal of said archwire in said archwire slot is facilitated and a closed position in which placement of said archwire in said archwire slot is inhibited.

Preferably, the spring element has turned free mesial and distal ends which are generally horizontal but are vertically offset with respect to one another. It is also preferred that the free mesial and distal ends are accommodated by bores formed in at least one wing and that the spring element is stressed when the free mesial and distal ends are accommodated by the bores. The free mesial and distal ends are offset in a labial-lingual plane in an unstressed condition.

In one embodiment, the body includes a pair of laterally spaced gingival tie wings and a pair of laterally spaced occlusal tie wings with each tie wing of one of the pairs of tie wings having a bore formed in an interior side surface thereof to accommodate one of the free mesial and distal ends of the spring element. The spring element may be generally cruciform or generally triangular in configuration.

In an alternative embodiment, the orthodontic bracket includes a single occlusal tie wing positioned between a pair of gingival tie wings. Opposed mesial and distal side surfaces of the occlusal tie wing have bores therein to accommodate the free mesial and distal ends of the spring element. In this case, the spring element is generally triangular in configuration.

In yet another embodiment, the free mesial and distal ends of the spring element are aligned along a common horizontal axis and the body includes a retaining clip to accommodate a gingival extension on the spring element to retain the spring element in the closed position.

In still yet another aspect of the present invention there is provided a pre-engaging orthodontic bracket for attaching an archwire to a tooth comprising:

a body having a lingual surface for attachment to a tooth, a pair of laterally spaced gingival tie wings and a pair of laterally spaced occlusal tie wings, said gingival and occlusal tie wings projecting from a labial surface of said body, both said gingival tie wings and occlusal tie wings being separated by an interwing region of said body;

an archwire slot extending mesiodistally across said body and between the gingival and occlusal tie wings to accommodate an archwire;

a locking shutter pivotally mounted on said body and being pivotable between an open position in which placement and removal of an archwire and said archwire slot is facilitated and a closed position in which placement of said archwire and said archwire slot is inhibited; and a slot activator pivotably mounted on said body and accommodated by a passage therein, said slot activator being pivotable to extend labially into said archwire slot to urge an archwire in said archwire slot towards said locking shutter.

Preferably, the slot activator is in the form of a spring element having turned free mesial and distal ends received by bores in the body. The bores are formed in opposed surfaces of the body defining opposed sides of the passage. The free mesial and distal ends of the spring element are out-turned and are accommodated by bores in the opposed surfaces.

Preferably, the free mesial and distal ends of the spring element are generally horizontal and are vertically offset with respect to one another. It is also preferred that the spring element is stressed when the free mesial and distal ends are accommodated by the bores and that the free mesial and distal ends are offset in a labial-lingual plane when the spring element is in an unstressed condition.

According to still yet another aspect of the present invention there is provided a body for an orthodontic bracket including a lingual surface for attachment to a tooth; a pair of laterally spaced gingival tie wings and a pair of laterally spaced occlusal tie wings, said gingival and occlusal tie wings projected from a labial surface of said body and being separated by an interwing region of said body; and an archwire slot extending mesiodistally across said body and between said gingival and occlusal tie wings wherein exterior mesial and distal side surfaces of said body are angulated with respect to an axis perpendicular to the longitudinal axis of said archwire slot, interior side surfaces of at least said occlusal tie wings being generally parallel to said axis.

In one embodiment, the interior side surfaces of the gingival tie wings are generally parallel to the axis while in another embodiment, the interior side surfaces of the gingival wings are angulated with respect to the axis.

The present invention provides a number of embodiments of orthodontic brackets which overcome disadvantages associated with prior art orthodontic brackets.

BRIEF DESCRIPTION OF THE DRAWINGS

FIG. 1d is front elevational view of the orthodontic bracket of FIG. 1a;

FIG. 2e is another front elevational view of the orthodontic bracket of FIG. 2a;

FIG. 3d is a front elevational view of the orthodontic bracket of FIG. 3a;

FIG. 4c is a front elevational view of the orthodontic bracket of FIG. 4a;

FIG. 4d is another side elevational view of the orthodontic bracket of FIG. 4a;

FIGS. 6b and 6c are perspective views of embodiments of retaining clips forming part of the orthodontic bracket of FIG. 6a;

FIG. 7b is a front perspective view of the orthodontic bracket of FIG. 7a;

FIG. 7c is a rear perspective view of the orthodontic bracket of FIG. 7a;

FIG. 8b is a side elevational view of the orthodontic bracket of FIG. 8a;

FIG. 9b is a side elevational view, partly in section, of the orthodontic bracket of FIG. 9a;

FIG. 9c is a top plan view of the orthodontic bracket of FIG. 9a;

FIG. 10c is top plan view of the orthodontic bracket of FIG. 10a;

FIG. 10d is a perspective view of the orthodontic bracket of FIG. 10a with the locking shutter pivoted to an open condition;

DETAILED DESCRIPTION OF THE PREFERRED EMBODIMENTS

Referring now to FIGS. 1a to 1e, a pre-engaging orthodontic bracket is shown and is generally indicated to by reference numeral 10. As can be seen, orthodontic bracket 10 includes a body 12 and a lingual mounting pad 14 attached to the body. The mounting pad 14 has a lingual surface to be attached to a tooth. A pair of laterally spaced gingival tie wings 16 and a pair of laterally spaced occlusal tie wings 18 extend from a labial surface of the body 12. The gingival tie wings 14 and the occlusal tie wings 18 curve lingually. An archwire slot 20 extends mesiodistally across the body 12 and between the gingival and occlusal tie wings 16 and 18. The archwire slot 20 opens labially to receive an archwire 22. The archwire slot 20 is interrupted in the interwing region 12' of the body.

A locking shutter 30 is pivotally mounted on the occlusal tie wings 18 and is moveable between a closed position where access to the archwire slot 20 is inhibited and an open position where access to the archwire slot 20 is permitted. In this embodiment, the locking shutter 30 is in the form of spring element having a generally cruciform outline. The locking shutter 30 has opposed free mesial and distal ends that are out-turned to define laterally spaced, oppositely directed tails 32 and 34 respectively. The tails 32 and 34 are generally horizontal but are vertically offset and are offset in a labial-lingual plane (see FIG. 1c). Each of the tails 32 and 34 is received in a respective bore 36 and 38 formed in one of the occlusal tie wings 18. The bores 36 and 38 are vertically offset from one another. Thus, the free mesial and distal ends of the locking shutter 30 are stressed when inserted into the bores 36 and 38 causing the locking shutter 30 to be naturally biased to the closed position shown in FIG. 1e. The tails 32 and 34 are free to rotate within the respective bores 36 and 38 to permit pivotal movement of the locking shutter 30 between the opened and closed positions.

Figure 1A:
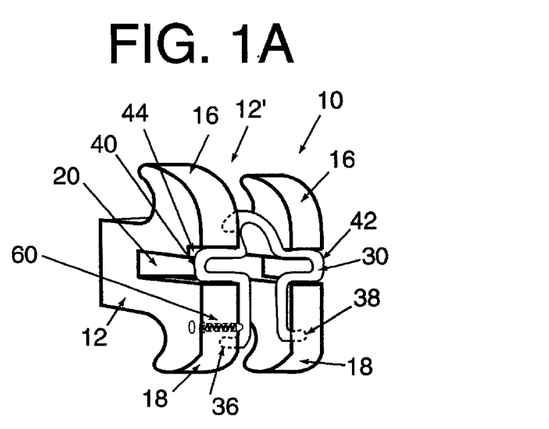
FIG. 1a is a perspective view of a pre-engaging orthodontic bracket in accordance with the present invention.

A stop 60 is provided on one of the occlusal tie wings 18 to inhibit inadvertent movement of the locking shutter 30 from a closed position to an open position and to maintain the locking shutter open when it is pivoted to the open position. The stop 60 includes a head 62 received in a bore 64 in the occlusal tie wing 18. A spring 66 acts between the head and the end of the bore 64 to bias the head to an outer extent adjacent the interior side surface of the occlusal tie wing. Abutments (not shown) are provided at the open end of the bore to inhibit removal of the head 62 from the bore 64. A nipple 68 is provided on the head 62 and extends into the space between the occlusal tie wings 18. The nipple 68 contacts a labial surface of the locking shutter 30 above the tail 32 when the locking shutter is in a closed position. Furthermore, the nipple 68 contacts a lingual surface of the locking shutter above the tail 32 when the locking shutter is in an open position to inhibit the locking shutter from accidentally closing during removal and replacement of an archwire 22 in the archwire slot 20.

The locking shutter 30 has a pair of oppositely directed arms 40 and 42 which extend across the archwire slot 20. A horizontal recess 44 is formed in each of the gingival tie wings 16 adjacent the archwire slot 20 to provide an abutment surface 46 which limits pivotal movement of the locking shutter 30 towards the archwire slot 20.

The locking shutter 30 also includes a gingival arm 50 which curves lingually to define a rearwardly projecting hook. A recess 52 is provided in the gingival surface of the body and defines a lip 54 on the gingival surface of the body 12 which passes through the gingival arm 50 when the locking shutter 30 is in the closed position to retain the locking shutter 30 in the closed position.

Figure 1B:
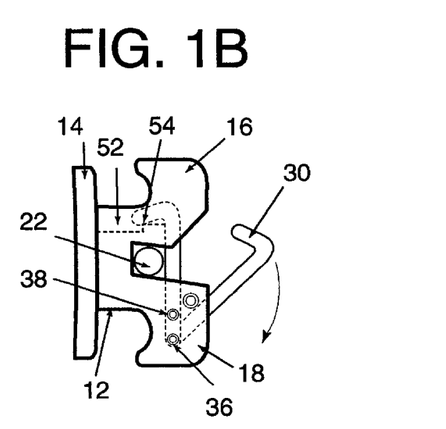
FIG. 1b is a side elevational view of the orthodontic bracket of FIG. 1a with a lingual mounting pad on the body of the orthodontic bracket.
Figure 1C:
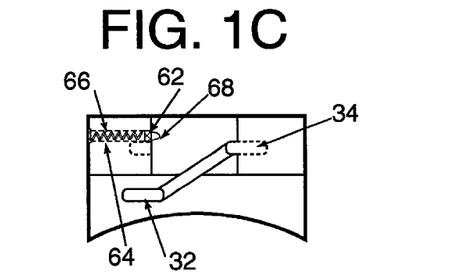
FIG. 1c is a bottom plan view of the orthodontic bracket of FIG. 1a with the locking shutter partially installed.
Figure 1D:
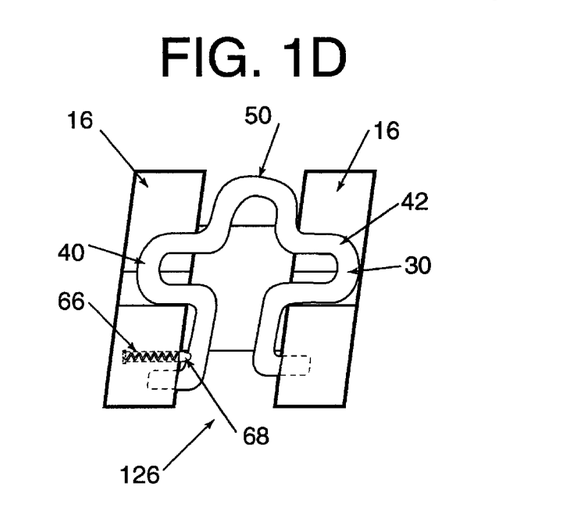
Figure 1E:
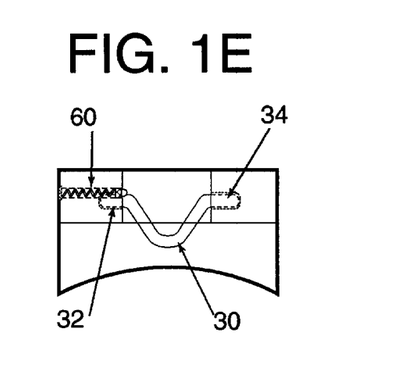
FIG. 1e is a bottom plan view of the orthodontic bracket of FIG. 1a with the locking shutter fully installed.

As can be seen in FIG. 1b, the lip 54 retains the locking shutter 30 against the archwire 22 and inhibits relative movement between the archwire 22 and the body 12 of the orthodontic bracket 10. To release the archwire 22, the locking shutter 30 is pivoted about the offset tails 32 and 34 to release the hook 50 from the extension 54. As the locking shutter is pivoted, the head 62 is pushed into the bore 64 against the bias of the spring 66.

The eccentricity of the axes of rotation of the tails 32 and 34 and the stress placed on the locking shutter by virtue of the vertically and labially-lingually offset tails, causes a torsional resistance due to the flexure of the spring element which biases the locking shutter 30 back towards the closed position. This movement of the locking shutter 30 is opposed until such time as the locking shutter goes over-center, at which point the locking shutter 30 becomes biased to the open position. However as mentioned above, the stop 60 inhibits the locking shutter 30 from moving back to the closed position prior to the locking shutter reaching the over-center position. In this way, the locking shutter 30 is resiliently biased towards the body 12 as it moves towards the closed position but remains in a stable open position at other times.

Referring now to FIGS. 2a to 2h another embodiment of pre-engaging orthodontic bracket 110 in accordance with the present invention is shown. In this embodiment, the locking shutter 130 is in the form of a generally triangular spring element having out-turned free mesial and distal ends defining laterally spaced tails 132 and 134. Each of the tails is pivotally received within a respective bore 136 and 138 formed in a respective one of the occlusal tie wings 118. The tails 132 and 134 are generally horizontal but are vertically offset and are offset in a labial-lingual plane (see FIG. 2c). The free mesial and distal ends of the spring element are stressed when inserted into the bores 136 and 138 causing the locking shutter 130 to be naturally biased to closed position shown in FIG. 2d.

Figure 2A:
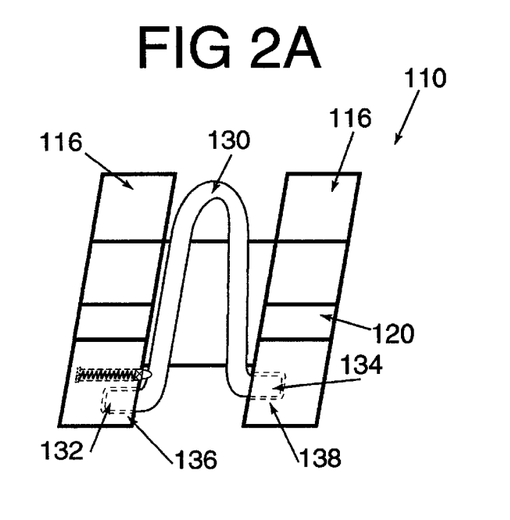
FIG. 2a is a front elevational view of an alternative embodiment of a pre-engaging orthodontic bracket in accordance with the present invention.
Figure 2B:
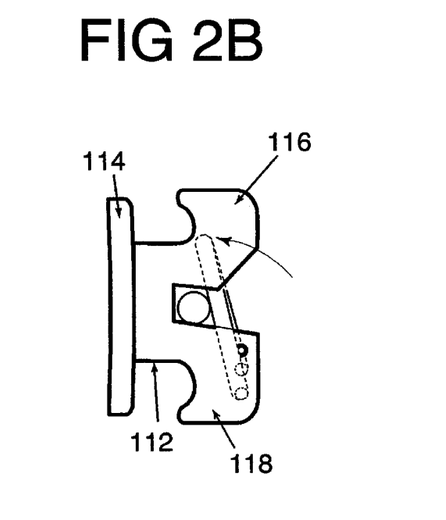
FIG. 2b is a side elevational view of the orthodontic bracket of FIG. 2a with a lingual mounting pad on the body of the orthodontic bracket.
Figure 2C:
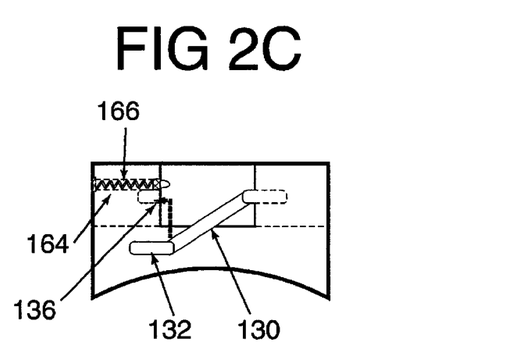
FIG. 2c is a bottom plan view of the orthodontic bracket of FIG. 2a with the locking shutter partially installed.
Figure 2D:
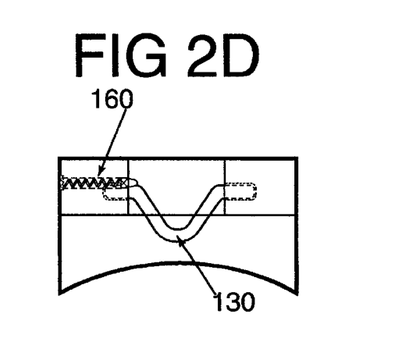
FIG. 2d is a bottom plan view of the orthodontic bracket of FIG. 2a with the locking shutter fully installed.
Figure 2E:
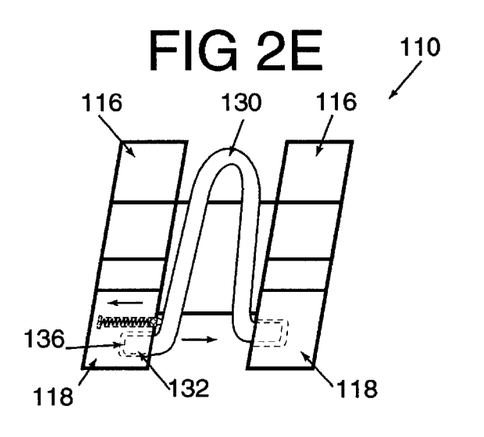
Figure 2F:
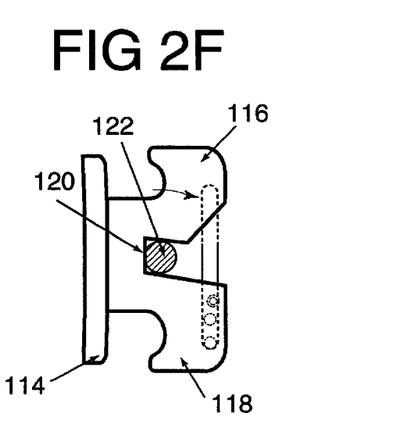
FIG. 2f is a side elevational view of the orthodontic bracket of FIG. 2a with the locking shutter pivoted towards an open condition.
Figure 2G:
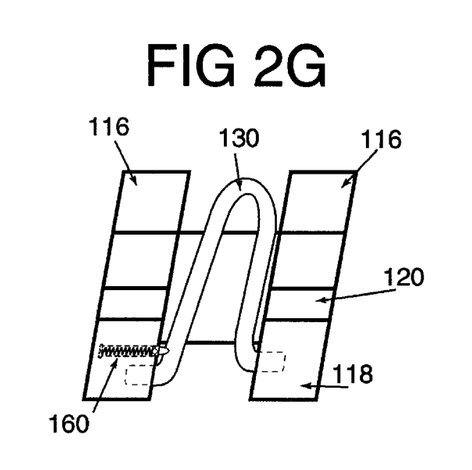
FIG. 2g is front elevational view of the orthodontic bracket of FIG. 2f.
Figure 2H:
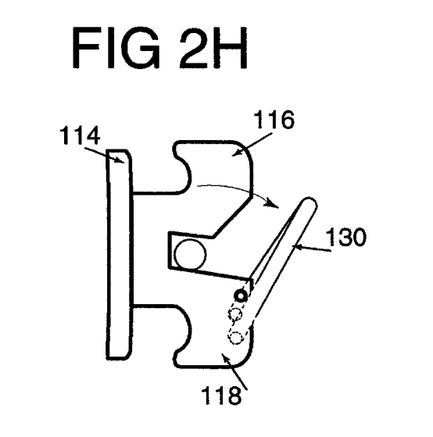
FIG. 2h is a side elevational view of the orthodontic bracket of FIG. 2a with the locking shutter pivoted to an open condition.

A stop 160 similar to that of the previous embodiment is provided on one of the occlusal tie wings 118 to inhibit inadvertent movement of the locking shutter 130 from a closed position to an open position and to maintain the locking shutter open when the locking shutter is pivoted to the open condition.

To open the orthodontic bracket 110, the locking shutter 130 is pivoted about the tails 132 and 134. As the locking shutter is pivoted, the head 162 of the stop 160 is pushed into the bore 164 against the bias of the spring 166. The reaction force applied to the locking shutter 130 by the stop 160 causes the tail 132 to move axially in a direction towards the interwing region 112' (see FIGS. 2e and 2g). When the locking shutter 130 is pivoted beyond the stop, the tail 132 snaps back into the bore and the head 162 is biased back to its outer extent by the spring 166. The stop 160 in this condition inhibits the locking shutter 130 from moving back towards the closed position. In this way, the archwire slot 120 remains open allowing an archwire 122 to be removed and/or inserted into the archwire slot.

Referring now to FIGS. 3a to 3e, yet another embodiment of a pre-engaging orthodontic bracket 210 is shown. As can be seen, in this embodiment a labial extension 270 is provided on body 212 in the interwing region 212' between the occlusal tie wings 218. Thus, the occlusal surface of the archwire slot 220 is continuous. The extension 270 projects labially beyond the occlusal tie wings 218.

Figure 3A:
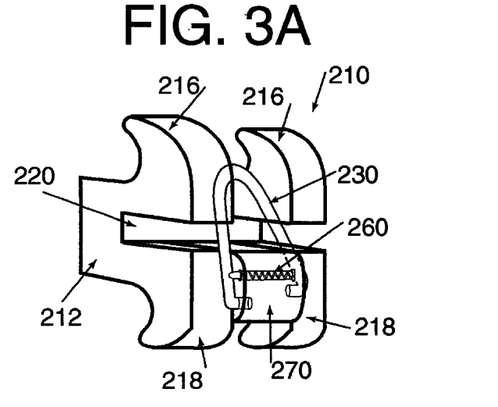
FIG. 3a is a perspective view of another embodiment of a pre-engaging orthodontic bracket in accordance with the present invention.
Figure 3B:
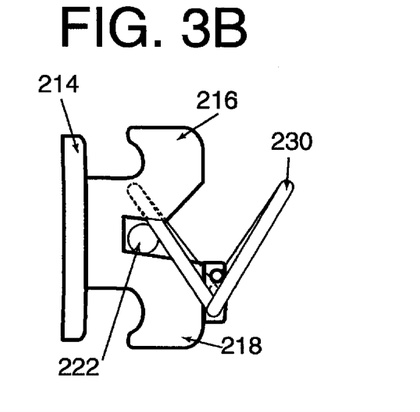
FIG. 3b is a side elevational view of the orthodontic bracket of FIG. 3a with a lingual mounting pad on the body of the orthodontic bracket.
Figure 3C:
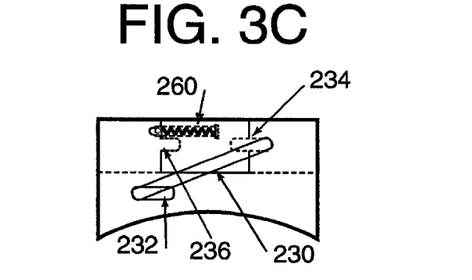
FIG. 3c is bottom plan view of the orthodontic bracket of FIG. 3a with the locking shutter partially installed.
Figure 3D:
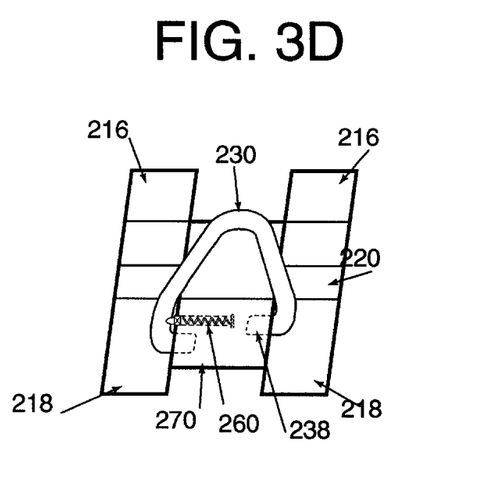
Figure 3E:
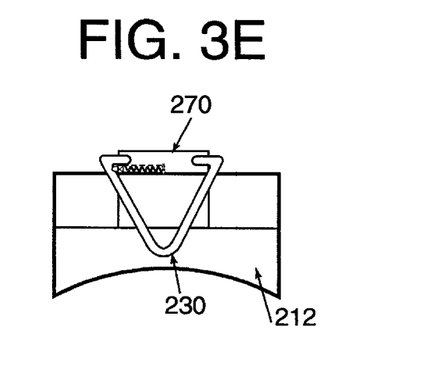
FIG. 3e is a bottom plan view of the orthodontic bracket of FIG. 3a with the locking shutter fully installed.
Figure 4A:
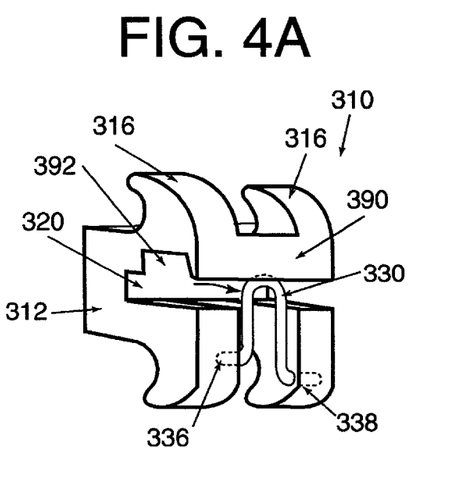
FIG. 4a is a perspective view of another embodiment of a pre-engaging orthodontic bracket in accordance with the present invention.
Figure 4B:
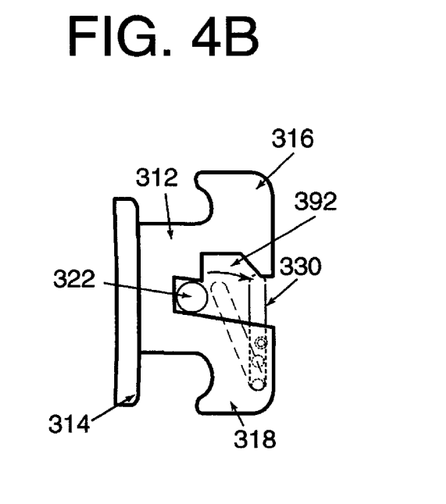
FIG. 4b is a side elevational view of the orthodontic bracket of FIG. 4a with a lingual mounting pad on the body of the orthodontic bracket.
Figure 4C:
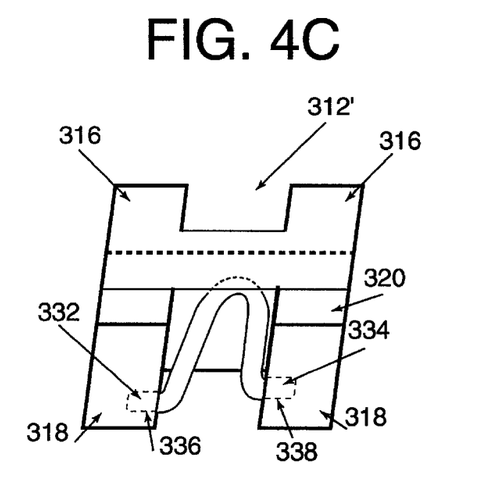
Figure 4D:
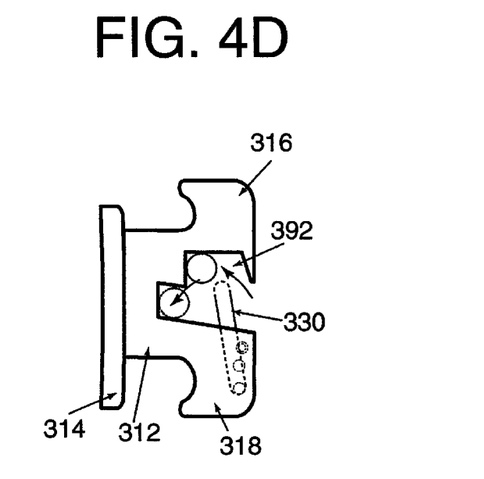

The locking shutter 230 is again in the form of a generally triangular spring element having opposed free mesial and distal ends which are turned to define laterally spaced inwardly directed tails 232 and 234. The tails 232 and 234 are generally horizontal but are vertically offset and are offset in a labial-lingual plane. The tails are received by vertically offset bores 236 and 238 formed in opposed mesial and distal side surfaces of the extension 270 and are free to rotate within the bores allowing the locking shutter 230 to pivot between closed and open positions. A stop 260 similar to that shown in the first embodiment is provided in the extension 270 to inhibit inadvertent movement of the locking shutter 230 from the closed position to the open position and to maintain the locking shutter 230 open when it is pivoted to the open position.

Referring now to FIGS. 4a to 4d, yet another embodiment of a pre-engaging orthodontic bracket 310 is shown. In this embodiment, the body 312 is not interrupted in the interwing region 312' between the gingival tie wings 316 and defines a bridge 390 which spans the gingival tie wings. A recess 392 is formed in the undersurface of the gingival tie wings 316 and the bridge 390. In this embodiment, the locking shutter 330 is in the form of a generally triangular spring element having out-turned free mesial and distal ends defining laterally spaced tails 332 and 334. Each of the tails is pivotally received within a respective bore 336 and 338 formed in the respective one of the occlusal tie wings 318. The tails 332 and 334 are generally horizontal but are vertically offset and are offset in a labially-lingual plane. The free mesial and distal ends of the locking shutter are stressed when inserted into the bores 336 and 338 causing the locking shutter 330 to be naturally biased away from the archwire slot 320 to the position shown in FIG. 4b. A stop 360 similar to that of the first embodiment is provided on one of the occlusal tie wings 318 to maintain the locking shutter 330 away from the labial surface of the recess 392 when the locking shutter 330 is pivoted towards the archwire slot 320.

Although the embodiments of FIGS. 1a to 3e show the stop as including a head having a nipple thereon, the head being biased to an outer extent by a spring, it should be apparent to those of skill in the art that alternative arrangements for the stop can be used. For example, the stop may be in the form of an integral projection on the orthodontic bracket. In this case, the projection contacts a labial surface of the locking shutter when the locking shutter is in the closed position. When the locking shutter is pivoted to an open position, the reaction of the locking shutter against the projection causes one of the tails of the locking shutter to move axially in a direction out of the bore allowing the locking shutter to move past the projection. Once the locking shutter has been pivoted to a point passed the projection, the tail of the locking shutter snaps back into the bore. In this position, the projection contacts a lingual surface of the locking shutter inhibiting the locking shutter from moving back to the closed position.

Figure 5A:
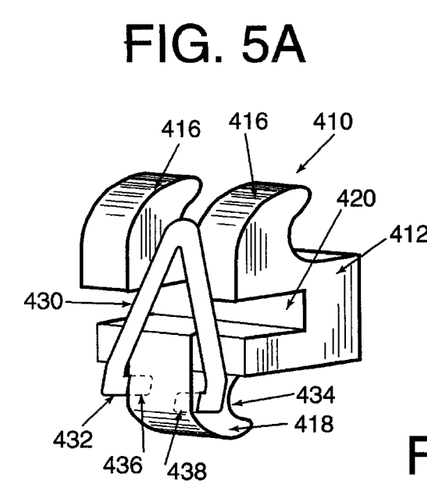
FIG. 5a is a perspective view of yet another embodiment of a pre-engaging orthodontic bracket in accordance with the present invention.
Figure 5B:
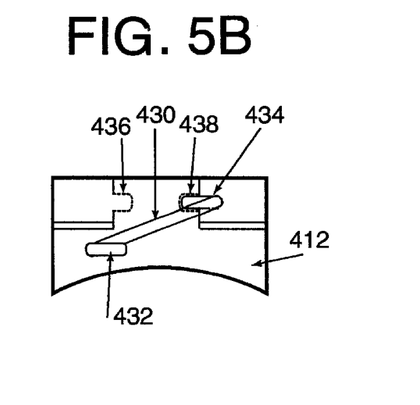
FIG. 5b is a bottom plan view of the orthodontic bracket of FIG. 5a with the locking shutter partially installed.

Referring now to FIGS. 5a and 5b, another embodiment of a pre-engaging orthodontic bracket is shown and is generally indicated to by reference numeral 410. In this embodiment, the orthodontic bracket includes a pair of laterally spaced gingival tie wings 416 and a single occlusal tie wing 418 extending from a labial surface of the body 412. The occlusal tie wing 418 has vertically offset bores 436 and 438 formed in its opposed mesial and distal side surfaces. A locking shutter 430 in the form of a generally triangular spring element having free mesial and distal ends defining in-turned tails 432 and 434 is pivotally mounted on the body. The tails 432 and 434 are generally horizontal but are vertically offset and are offset in a labial-lingual plane. The tails are received by vertically offset bores 436 and 438 formed in opposed mesial and distal side surfaces of the occlusal tie wing 418 and are free to rotate within the bores allowing the locking shutter 430 to pivot between opened and closed positions.

Figure 6A:
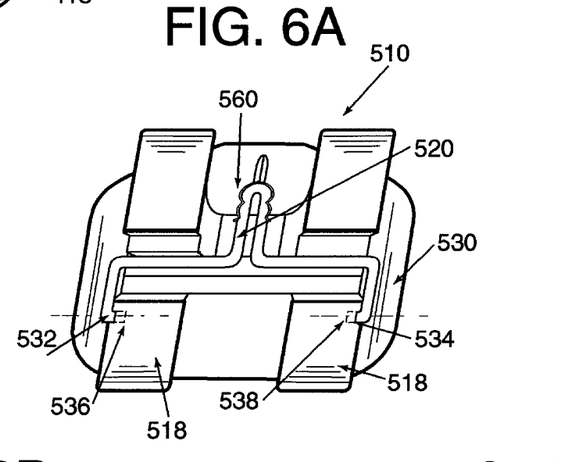
FIG. 6a is front elevational view of still yet another embodiment of a pre-engaging orthodontic bracket in accordance with the present invention.
Figure 6B:
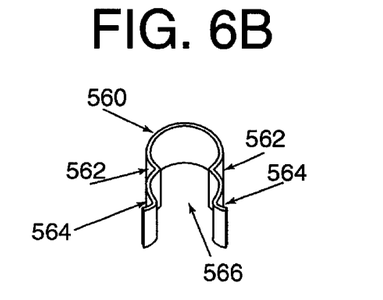
Figure 6C:
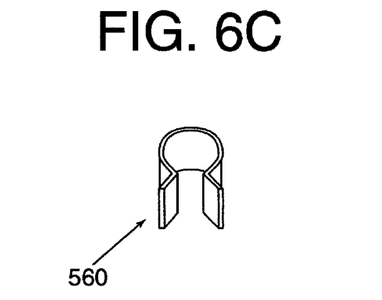

Referring to FIGS. 6a and 6b, an alternative embodiment of a pre-engaging orthodontic bracket 510 is shown. In this embodiment, the locking shutter 530 is in the form of a wire loop having in-turned free distal ends defining laterally spaced tails 532 and 534. Each of the tails is pivotally received within a respective bore 536 and 538 formed in a respective one of the occlusal tie wings 518. The tails 532 and 534 are pivotal within the bores and are aligned on a common horizontal axis. The locking shutter 530 includes a narrow gingival extension 550 which is received within a locking clip 560 mounted on the body 512 between the gingival tie wings 516.

As can be best seen in FIG. 6b, locking clip 560 is generally U-shaped with serpentine limbs 562 terminating in outwardly-flared ends 564. The extension 550 is received between the flared ends 564 to force the limbs 562 apart until the extension 550 is accommodated in the cylindrical passage 566. At that time, the limbs 562 move back together to retain the extension 550. The locking clip 560 may alternatively have a generally circular section as shown in FIG. 6b.

Figure 7A:
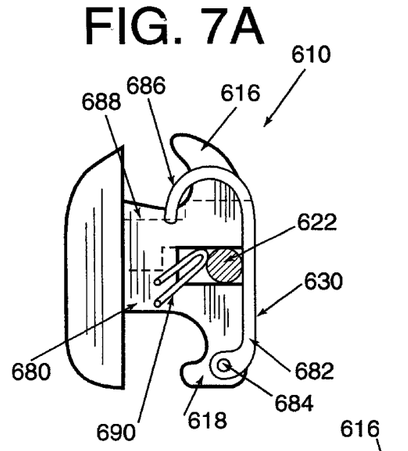
FIG. 7a is a side elevational view of still yet another embodiment of a pre-engaging orthodontic bracket in accordance with the present invention.
Figure 7B:
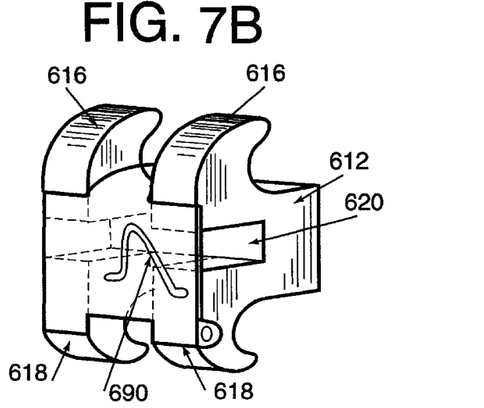
Figure 7C:
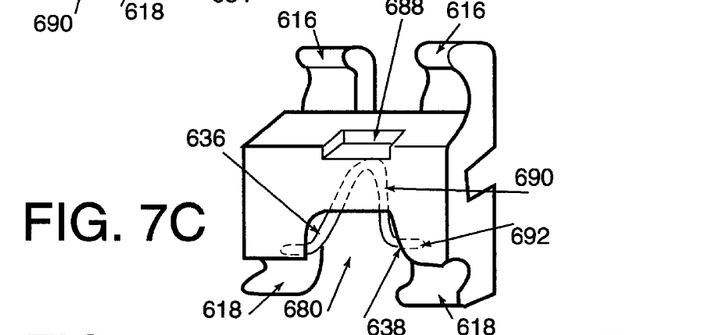

Referring now to FIGS. 7a to 7c, still yet another embodiment of a pre-engaging orthodontic bracket 610 is shown. The orthodontic bracket 610 includes a body 612 having a labial surface from which a pair of laterally spaced gingival tie wings 616 and a pair of laterally spaced occlusal tie wings 618 extend. A stepped passage 680 is provided in the body 612 between the occlusal tie wings 618. Bores 636 and 638 formed in opposed surfaces of the body 612 defining opposed sides of the passage 680.

A pivotable locking shutter 630 has an occlusal arm 682 which encircles a pivot pin 684 extending between the occlusal tie wings 618. The locking shutter 630 also has a gingival arm 686 which curves lingually and occlusially. The gingival arm 686 co-operates with a recess 688 formed in the body 612 to retain the locking shutter 630 in a closed position. An aperture (not shown) is provided through the locking shutter 630 to accommodate a tool so that a labially directed force can be applied to the locking shutter using the tool to release the gingival arm 686 of the locking shutter from the recess 688.

A slot activator 690 in the form of a generally triangular spring element having out-turned, laterally spaced free mesial and distal ends defining generally horizontal tails 692 is pivotally mounted on the body 612 within the passage 680. The tails 692 are vertically offset and are also offset in a labial-lingual plane. The tails 692 are received in vertically offset bores 636 and 638 and are free to rotate therein. The slot activator 690 is pivotable within the passage 680 towards and into the archwire slot 620 to apply a bias to an archwire 622 in the archwire slot urging the archwire towards the locking shutter 630.

Figure 8A:
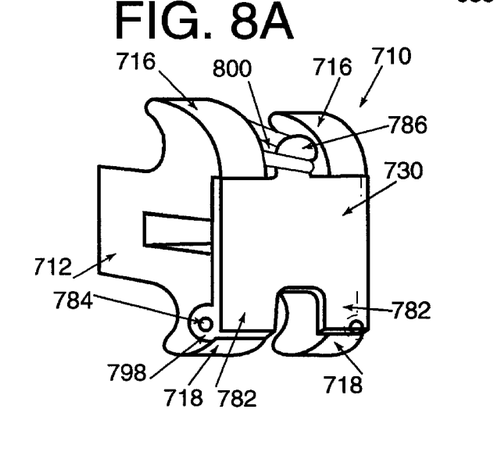
FIG. 8a is perspective view of still yet another embodiment of a pre-engaging orthodontic bracket in accordance with the present invention.
Figure 8B:
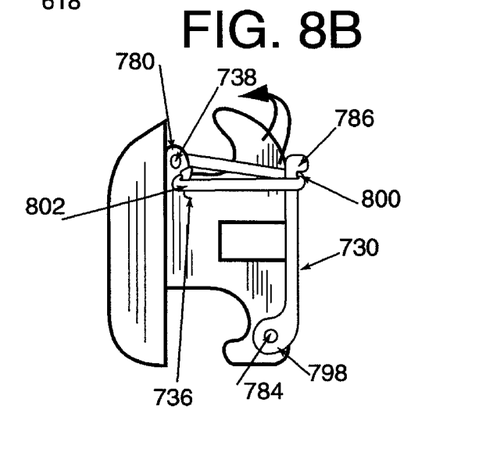

Referring to FIGS. 8a and 8b, still yet another embodiment of a pre-engaging orthodontic bracket 710 is shown. The orthodontic bracket 710 includes a body 712 having a labial surface from which a pair of laterally spaced gingival tie wings 716 and a pair of laterally spaced occlusal tie wings extend. An extension 780 projects gingivally from the gingival surface of the body 712 and has bores 736 and 738 formed in its opposed mesial and distal side surfaces.

A pivotal locking shutter 730 is mounted on the orthodontic bracket 710 and includes a pair of laterally spaced occlusal arms 782, each of which overlies one of the occlusal tie wings 718. A flange 798 extends lingually from each occlusal arm 782 and overlies an outer side surface of a respective one of the occlusal tie wings 718. The flanges 798 accommodated pivot pins 784 extending from the occlusal tie wings 718. A gingivally extension 786 is also provided on the locking shutter 730.

A lock 800 in the form of a generally triangular spring element is pivotally mounted on the extension 780. The lock 800 has in-turned laterally offset, free mesial and distal ends defining tails 802 which are received in the bores 736 and 738. The tails 802 are free to rotate in the bores to allow the lock 800 to pivot downwardly over the extension 786 to retain the locking shutter 730 in a closed position. If desired, the locking shutter 730 can be in the form of a spring element such as that shown in FIG. 3a. In this case, the lock 800 will surround the apex of the locking shutter to retain the locking shutter 730 in a closed position.

Figure 9A:
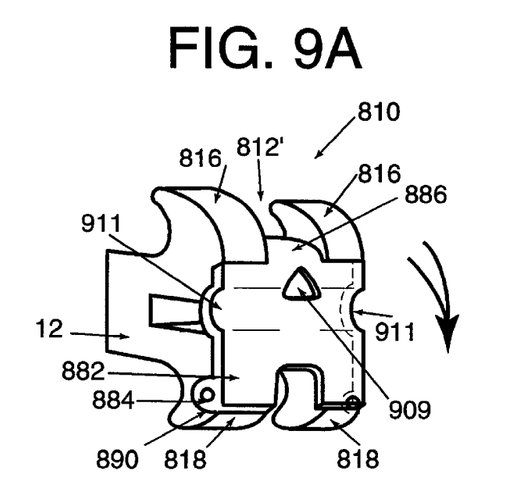
FIG. 9a is a perspective view of still yet another embodiment of a pre-engaging orthodontic bracket in accordance with the present invention.
Figure 9B:
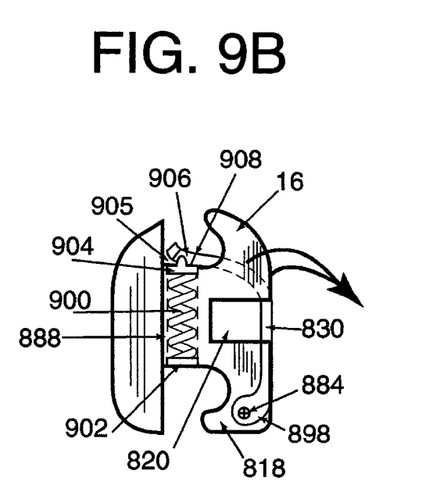
Figure 9C:
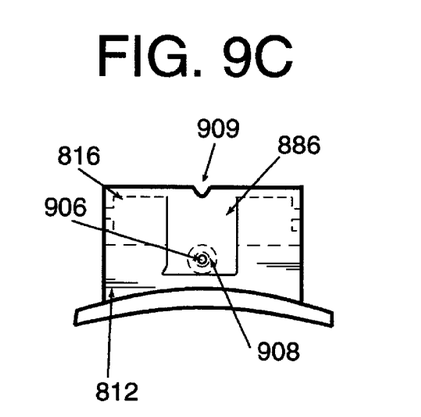

Referring now to FIGS. 9a to 9c, still yet another embodiment of a pre-engaging orthodontic bracket 810 is shown. In this embodiment, the orthodontic bracket 810 includes a body 812 having a labial surface from which a pair of laterally spaced gingival tie wings 816 and a pair of laterally spaced occlusal tie wings 818 extend. A vertical passage 888 is provided in the body 812 and accommodates a coil spring 900. Coil spring 900 acts between a stop 902 secured to the body 812 at the bottom of the passage 888 and a head 904 moveable within the passage. Abutments 905 at the top of the passage 888 inhibit the head 904 from moving out of the passage 888. The head 904 has a gingivally extending nipple 906 thereon which extends out of the passage above the gingival surface of the body 812.

A pivotable locking shutter 830 is mounted on the orthodontic bracket 810 and includes a pair of laterally spaced occlusal arms 882, each of which overlies one of the occlusal tie wings 818. A flange 898 extends lingually from each occlusal arm 882 and overlies an outer side surface of a respective one of the occlusal tie wings 818. The flanges 898 accommodate pivot pins 884 extending from the occlusal tie wings.

The locking shutter 830 also includes a gingival arm 886 which curves lingually to overlie the gingival surface of the body 812 in the interwing region 812'. A hole 908 is provided in the gingival arm 886 near its lingual end. Hole 908 accommodates the nipple 906 on head 904 to retain the shutter 830 in a closed position. The head 904 can be pushed into the passage 888 to remove the nipple 906 from the hole 908 allowing the locking shutter 830 to pivot about pivot pins 884 to an open position.

Locking shutter 830 further includes a generally triangular aperture 909 therein to accommodate a tool so that a labially directed force can be applied to the locking shutter using the tool to release the gingival arm 886 from the nipple 906 without requiring the head 904 to be manually pushed into the passage 888. Depressions 911 are formed in locking shutter 830 so that the locking shutter extends into the archwire slot 820 at its opposed mesial and distal ends.

Figure 10A:
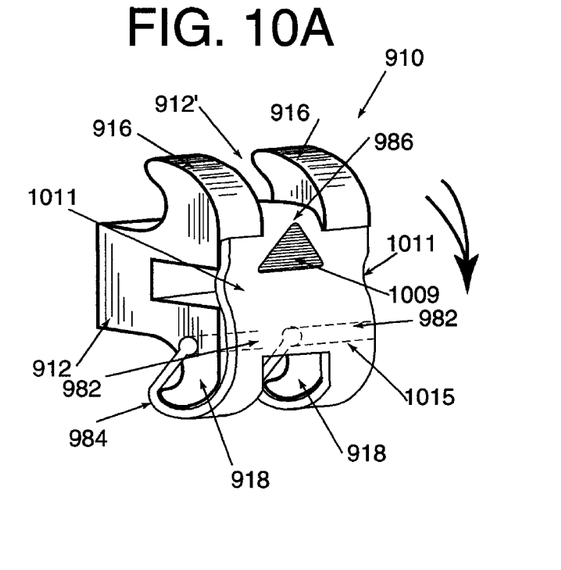
FIG. 10a is a perspective view of still yet another embodiment of a pre-engaging orthodontic bracket in accordance with the present invention.
Figure 10B:
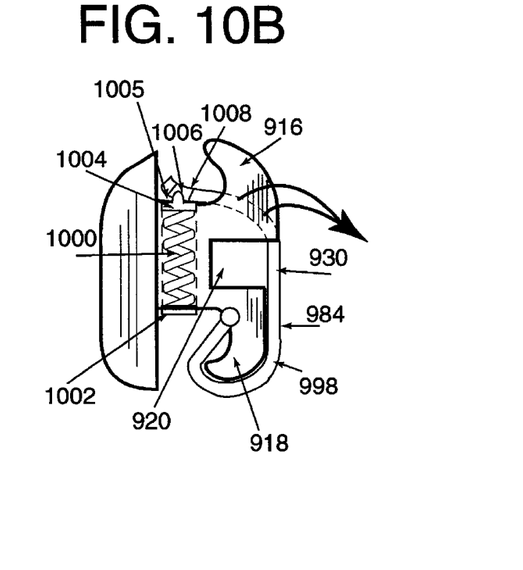
FIG. 10b is a side elevational view of the orthodontic bracket of FIG. 10a with a lingual mounting pad on the body of the orthodontic bracket.
Figures 10C, 10D:
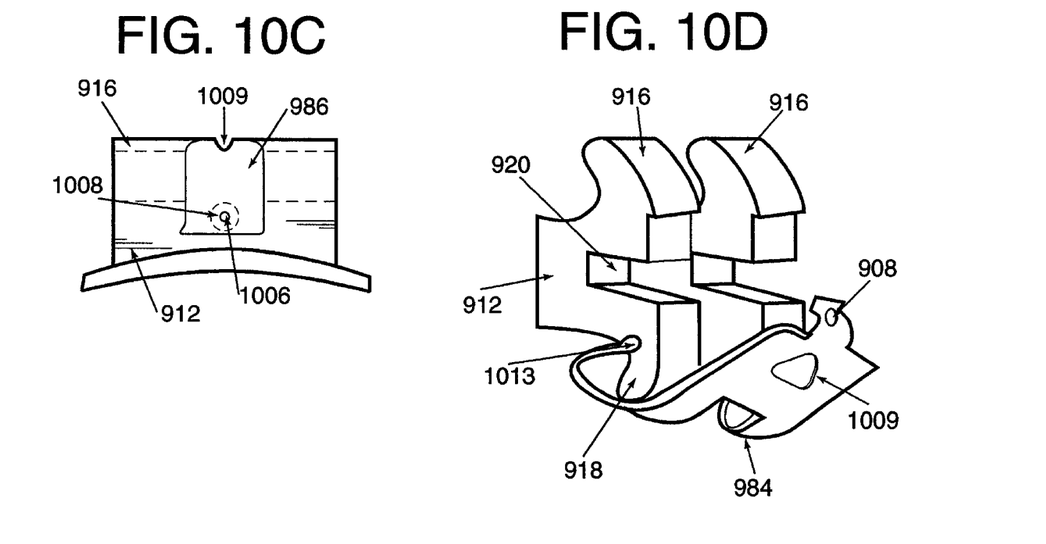

Referring now to FIGS. 10a to 10d, still yet another embodiment of a pre-engaging orthodontic bracket 910 in accordance with the present invention is shown. The orthodontic bracket 910 is very similar to the embodiment of FIGS. 9a to 9c. However, in this embodiment, the occlusal arms 982 of the locking shutter 930 curve around the occlusal tie wings 918 and have ball shaped formations 1000 at their free ends. The formations 1013 are received by undercuts 1015 formed in the occlusal tie wings 918. When the locking shutter 930 is pivoted from a closed position to an open position, the locking shutter 930 rotates and translates about the occlusal tie wings 918 as shown in FIG. 10d.

Figure 11A:
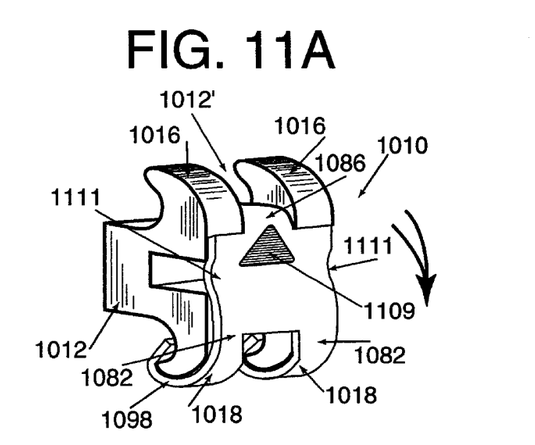
FIG. 11a is a perspective view of still yet another alternative embodiment of a pre-engaging orthodontic bracket in accordance with the present invention.
Figure 11B:
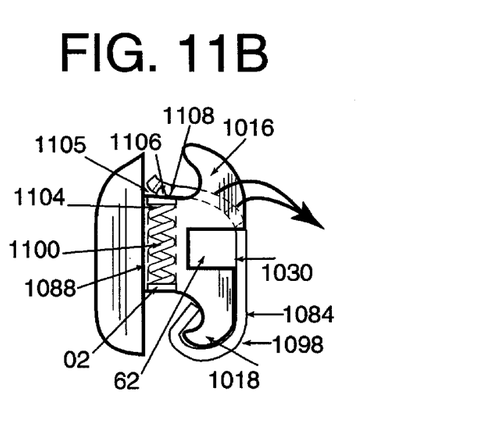
FIG. 11b is a side elevational view of the orthodontic bracket of FIG. 11a with a lingual mounting pad on the body of the orthodontic bracket.

Referring now to FIGS. 11a and 11b, still yet another embodiment of a pre-engaging orthodontic bracket 1010 is shown. The orthodontic bracket 1010 is similar to that of the previous embodiment. However, in this case, the free ends of the occlusal arms 1082 of the locking shutter 1030 do not terminate in ball shaped formations. Rather, the occlusal arms 1082 of the locking shutter 1030 are configured so that the free ends contact the undersurface of the body 1012 when the locking shutter is in the closed position leaving a gap between the occlusal arms 1082 of the locking shutter and the lingual surfaces of the occlusal tie wings 1018. When the locking shutter 1030 is pivoted to the open position, the locking shutter rotates and translates about the occlusal tie wings 1018.

Figures 12A, 12B:
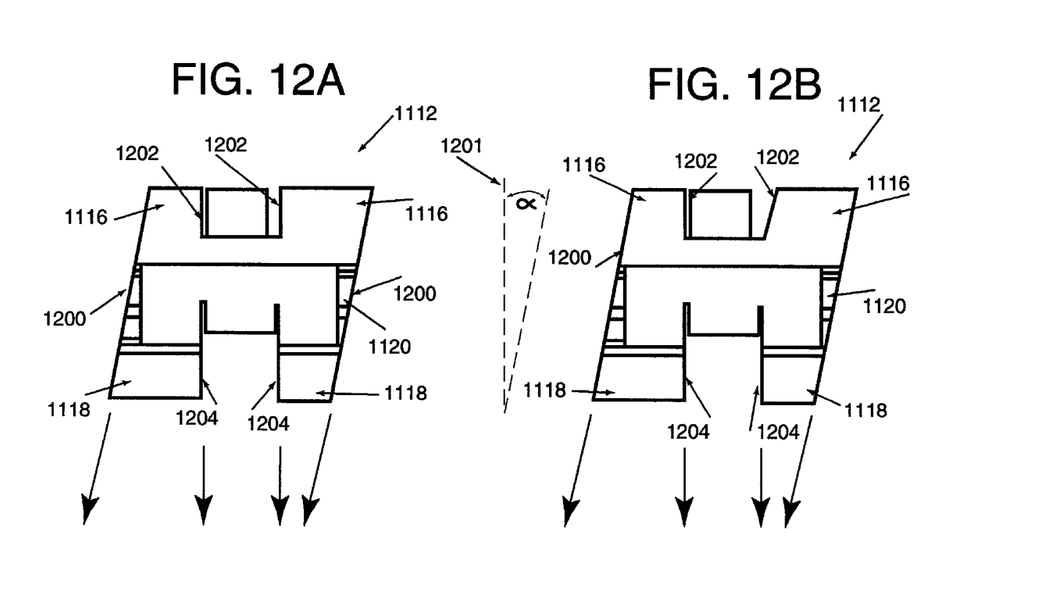
FIGS. 12a and 12b are front elevational views of alternative embodiments of a body for an orthodontic bracket.

Referring to FIGS. 12a and 12b, alternative embodiments of a body 1112 for an orthodontic bracket are shown. The orthodontic bracket body designs facilitate the manufacture of locking shutters for the orthodontic brackets. In the embodiment of FIG. 12a, the outer mesial and distal side surfaces 1200 of the orthodontic bracket body 1112 are angulated with respect to an axis 1201 perpendicular to the longitudinal axis of the archwire slot 1120. However, the interior side surfaces 1202 and 1204 of the gingival and occlusal tie wings 1116 and 1118 are generally parallel to the axis 1201. In the embodiment of FIG. 12b, the interior side surfaces 1202 of the gingival tie wings 1116 are angulated with respect to the axis 1201 while the interior side surfaces of the occlusal tie wings 1118 are parallel to the axis 1201. The angulated side surfaces of the body 1112 form an angle α with the axis 1201 equal to approximately 10 degrees.

The interior side surfaces of the occlusal tie wings 1118 allow locking shutters having straight occlusal and gingival arms to be mounted on the body regardless of the angulation of the exterior mesial and distal side surfaces of the body. Manufacturing straight locking shutters with external surfaces parallel to the axis 1201 is simpler than manufacturing locking shutters with angulated external surfaces. This of course helps to reduce manufacturing costs.

Although preferred embodiments of the present invention have been described, those of skill in the art will appreciate that variations and modifications may be made without departing from the spirit and scope thereof as defined by the appended claims.

I claim:

1. A pre-engaging orthodontic bracket for attaching an archwire to a tooth comprising:
    a body having a lingual surface for attachment to a tooth, a pair of laterally spaced gingival tie wings and a pair of laterally spaced occlusal tie wings, said gingival and occlusal tie wings projecting from a labial surface of said body, both said gingival tie wings and occlusal tie wings at opposed mesial and distal sides of said body being separated by an interwing region of said body, each of the gingival and occlusal tie wings having an inner side surface and an outer side surface;
    at least one pivot pin extending from one of said side surfaces of one of the tie wings;
    an archwire slot extending mesiodistally across said body and between the gingival and occlusal tie wings to accommodate an archwire; and
    a unitary locking shutter pivotal about said at least one pivot pin between an open position in which placement and removal of said archwire in said archwire slot is facilitated and a closed position in which placement of said archwire in said archwire slot is inhibited.

2. The orthodontic bracket as defined in claim 1 wherein a pair of pivot pins extend from one of the inner side surfaces and the outer side surfaces of one of the pair of occlusal tie wings and the pair of gingival tie wings, the locking shutter including a pair of laterally spaced flanges thereon, each of said flanges overlying a side surface of a respective one of said pairs of tie wings, said flanges accommodating the pivot pins extending from said one pair of tie wings.

3. An orthodontic bracket as defined in claim 2 further including a locking mechanism to retain said locking shutter in said closed position.

4. An orthodontic bracket as defined in claim 3 wherein said locking mechanism is in the form of a spring element mounted on said body, said spring element being pivotable to surround a gingival extension on said locking shutter and retain said locking shutter in said closed position.

5. An orthodontic bracket as defined in claim 4 wherein said spring element is generally triangular and is pivotably mounted on a gingival extension on said body adjacent said lingual surface.

6. An orthodontic bracket as defined in claim 5 wherein said spring element has in-turned distal ends accommodated by bores in said gingival extension, said in-turned ends being generally horizontal and vertically offset with respect to one another.

7. An orthodontic bracket as defined in claim 4 wherein said locking shutter includes a gingival arm overlying a gingival surface of said body when said locking shutter is in said closed position and wherein said locking mechanism is in the form of a head extending gingivally from said gingival surface, said head being accommodated by a hole in said gingival arm when said locking shutter is in said closed position.

8. An orthodontic bracket as defined in claim 7 wherein said head is accommodated within a passage formed in said body, said head being biased towards said gingival surface by a spring within said passage, said head having a nipple thereon extending beyond said passage and being accommodated by said hole.

9. An orthodontic bracket as defined in claim 8 wherein said locking shutter further includes an opening therein to accommodate a tool to facilitate pivoting of said locking shutter from said closed position to said open position.

10. A pre-engaging orthodontic bracket for attaching an archwire to a tooth comprising:
    a body having a lingual surface for attachment to a tooth, at least one gingival tie wing and at least one occlusal tie wing, said gingival and occlusal tie wings projecting from a labial surface of said body;
    an archwire slot extending mesiodistally across said body between said gingival and at least one occlusal tie wing to accommodate an archwire; and
    a locking shutter in the form of a spring element pivotally mounted on said body said spring element being pivotable between an open position in which placement and removal of said archwire in slot is facilitated and a closed position in which placement of said archwire in said archwire slot is inhibited, said spring element having turned distal ends, said distal ends being generally horizontal and vertically offset with respect to one another.

11. An orthodontic bracket as defined in claim 10 wherein said distal ends are accommodated by bores formed in at least one tie wing and wherein said spring element is stressed when said distal ends are in said bores, said distal ends also being offset in a labial-lingual plane in an unstressed condition.

12. An orthodontic bracket as defined in claim 11 wherein said body includes a pair of laterally spaced gingival tie wings and a pair of laterally spaced occlusal tie wings, each tie wing of one of said pair of tie wings having a bore formed in an interior side surface thereof to accommodate one of said distal ends.

13. An orthodontic bracket as defined in claim 11 wherein said orthodontic bracket includes a single occlusal tie wing positioned between a pair of gingival tie wings, opposed mesial and distal side surfaces of said occlusal tie wing having bores therein to accommodate said distal ends, said spring element being generally triangular in configuration.

14. An orthodontic bracket as defined in claim 11 wherein said body includes a pair of laterally spaced gingival tie wings and a pair of laterally spaced occlusal tie wings and a labial extension on said body between one of said pairs of tie wings, opposed mesial and distal side surfaces of said labial extension having bores therein to accommodate said distal ends.

15. An orthodontic bracket as defined in claim 10 wherein said turned ends are aligned along said common axis, said body further including a retaining clip thereon to accommodate a gingival extension on said locking shutter to retain said locking shutter in said closed position.

16. A pre-engaging orthodontic bracket for attaching an archwire to a tooth comprising:

a body having a lingual surface for attachment to a tooth, a pair of laterally spaced gingival tie wings and a pair of laterally spaced occlusal tie wings, said gingival and occlusal tie wings projecting from a labial surface of said body, both said gingival tie wings and occlusal tie wings being separated by an interwing region of said body;

an archwire slot extending mesiodistally across said body and between the gingival and occlusal tie wings to accommodate an archwire;

a locking shutter pivotally mounted on said body and being pivotable between an open position in which placement and removal of an archwire and said archwire slot is facilitated and a closed position in which placement of said archwire and said archwire slot is inhibited; and a slot activator pivotably mounted on said body and accommodated by a passage therein, said slot activator being pivotable to extend labially into said archwire slot to urge an archwire in said archwire slot towards said locking shutter.

17. An orthodontic bracket as defined in claim 16 wherein said slot activator is in the form of a spring element, said spring element having turned distal ends received by bores in said body.

18. An orthodontic bracket as defined in claim 17 wherein said bores are formed in opposed surfaces of said body defining opposed sides of said passage, said distal ends being out-turned and accommodated by said bores.

19. An orthodontic bracket as defined in claim 18 wherein said distal ends are generally horizontal and vertically offset with respect to one another.

20. An orthodontic bracket as defined in claim 19 wherein said spring element is stressed when said distal ends are in said bores, said distal ends also being offset in a labial-lingual plane in an unstressed condition.

21. An orthodontic bracket as defined in claim 18 wherein said spring element is generally triangular in configuration.

22. A body for an orthodontic bracket including a lingual surface for attachment to a tooth; a pair of laterally spaced gingival tie wings and a pair of laterally spaced occlusal tie wings, said gingival and occlusal tie wings projecting from a labial surface of said body and being separated by an interwing region of said body; and an archwire slot extending mesiodistally across said body and between the gingival and occlusal tie wings wherein exterior mesial and distal side surfaces of said body are angulated with respect to an axis perpendicular to the longitudinal axis of said archwire slot, interior side surfaces of at least said occlusal tie wings being generally parallel to said axis perpendicular to the longitudinal axis of said archwire slot, the interior side surfaces of said gingival tie wings being angulated with respect to said axis perpendicular to the longitudinal axis of said archwire slot.

* * * * *